(12) United States Patent
Heide et al.

(10) Patent No.: US 12,186,471 B2
(45) Date of Patent: Jan. 7, 2025

(54) DEVICE INCLUDING A DEVICE FOR DETERMINING A CHARACTERISTIC OF THE DEVICE

(71) Applicant: Fresenius Medical Care Deutschland GmbH, Bad Homburg (DE)

(72) Inventors: Alexander Heide, Eppstein (DE); Dejan Nikolic, Bad Soden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 734 days.

(21) Appl. No.: 16/495,541

(22) PCT Filed: Mar. 20, 2018

(86) PCT No.: PCT/EP2018/057057
§ 371 (c)(1),
(2) Date: Sep. 19, 2019

(87) PCT Pub. No.: WO2018/172372
PCT Pub. Date: Sep. 27, 2018

(65) Prior Publication Data
US 2021/0283322 A1    Sep. 16, 2021

(30) Foreign Application Priority Data
Mar. 24, 2017 (DE) .......................... 102017106404.4

(51) Int. Cl.
*A61M 1/36* (2006.01)
*A61M 1/16* (2006.01)
(Continued)

(52) U.S. Cl.
CPC .......... *A61M 1/367* (2013.01); *A61M 1/3413* (2013.01); *A61M 1/36222* (2022.05);
(Continued)

(58) Field of Classification Search
None
See application file for complete search history.

(56) References Cited

U.S. PATENT DOCUMENTS

| 4,397,194 A | 8/1983 | Soltz |
|---|---|---|
| 6,598,487 B1 | 7/2003 | Marsh |

(Continued)

FOREIGN PATENT DOCUMENTS

| CN | 101371127 | 2/2009 |
|---|---|---|
| CN | 101421601 | 4/2009 |

(Continued)

OTHER PUBLICATIONS

International Preliminary Report on Patentability in Application No. PCT/EP2018/057057, dated Sep. 24, 2019, 9 pages (English Translation).

(Continued)

*Primary Examiner* — Jonathan M Peo
(74) *Attorney, Agent, or Firm* — Fish & Richardson P.C.

(57) ABSTRACT

The present disclosure relates to a medical device with respectively at least one hard part with fluid paths for guiding a medical fluid, for example, blood, through the hard part. The medical device also includes a converter and a device for determining a characteristic of the device. The converter is arranged to measure the characteristic of the fluid, while the fluid is present in one of the fluid paths. The characteristic may be geometric characteristic, for example, a fluid path.

20 Claims, 4 Drawing Sheets

(51) Int. Cl.
*A61M 1/34* (2006.01)
*H10N 30/00* (2023.01)
*H10N 30/857* (2023.01)

(52) U.S. Cl.
CPC ......... *H10N 30/101* (2024.05); *H10N 30/857* (2023.02); *A61M 1/16* (2013.01); *A61M 1/36224* (2022.05); *A61M 1/36226* (2022.05); *A61M 2205/0227* (2013.01); *A61M 2205/0233* (2013.01); *A61M 2205/0294* (2013.01); *A61M 2205/12* (2013.01); *A61M 2205/3317* (2013.01); *A61M 2205/3327* (2013.01); *A61M 2205/3331* (2013.01); *A61M 2205/3334* (2013.01)

(56) References Cited

U.S. PATENT DOCUMENTS

| | | | |
|---|---|---|---|
| 2003/0042181 A1* | 3/2003 | Metzner | A61M 1/3609 210/85 |
| 2004/0154409 A1* | 8/2004 | Stange | G01F 1/584 73/861.12 |
| 2005/0230292 A1* | 10/2005 | Beden | A61M 1/15632 210/321.71 |
| 2008/0184811 A1 | 8/2008 | Stange | |
| 2009/0101550 A1* | 4/2009 | Muller | A61M 1/1658 210/87 |
| 2009/0118667 A1 | 5/2009 | Haueter et al. | |
| 2011/0214504 A1* | 9/2011 | Bradley | G01L 19/14 73/723 |
| 2014/0263064 A1 | 9/2014 | Jones et al. | |
| 2015/0100014 A1 | 4/2015 | Uchiyama et al. | |
| 2017/0014899 A1 | 1/2017 | Schaechtl et al. | |
| 2018/0093029 A1 | 4/2018 | Abel et al. | |

FOREIGN PATENT DOCUMENTS

| | | |
|---|---|---|
| CN | 102525445 | 7/2012 |
| CN | 105873695 | 8/2016 |
| DE | 19605652 | 8/1997 |
| DE | 102009018664 A1 | 10/2010 |
| DE | 102010047248 | 4/2012 |
| DE | 102015104430 | 9/2016 |
| EP | 2559656 A1 | 2/2013 |
| JP | S57-501665 | 9/1982 |
| JP | H10-52490 | 2/1998 |
| JP | 2002-099330 | 4/2002 |
| JP | 2003-344126 | 12/2003 |
| JP | 2008-539924 | 11/2008 |
| JP | 2009-508116 | 2/2009 |
| JP | 2009-525770 | 7/2009 |
| JP | 2014-083092 | 5/2014 |
| JP | 2015-070934 | 4/2015 |
| WO | WO 82/01122 | 4/1982 |
| WO | WO 2006/120464 | 11/2006 |
| WO | WO 2007/031053 | 3/2007 |
| WO | WO 2007/095597 | 8/2007 |

OTHER PUBLICATIONS

International Search Report and Written Opinion in Application No. PCT/EP2018/057057, dated May 22, 2018, 9 pages (English Translation).

* cited by examiner

DEVICE INCLUDING A DEVICE FOR DETERMINING A CHARACTERISTIC OF THE DEVICE

CROSS-REFERENCE TO RELATED APPLICATIONS

The present application is the national stage entry of International Patent Application No. PCT/EP2018/057057, filed on Mar. 20, 2018, and claims priority to Application No. DE 10 2017 106 404.4, filed in the Federal Republic of Germany on Mar. 24, 2017, the disclosure of which are expressly incorporated herein in entirety by reference thereto.

TECHNICAL FIELD

The present disclosure relates to a device, in particular a medical device. It also relates to a method, an evaluation unit, and a treatment apparatus.

BACKGROUND

Prior art blood treatment apparatuses are connected to at least one medical device for blood treatment. Such a connected medical device may be a blood cassette, in which blood is treated or temporarily stored. Some of the connected medical devices are disposable.

SUMMARY

A device, in particular a medical device, is specified herein as having at least one hard part with complete or incomplete fluid paths, to guide a fluid, in particular a medical fluid, in particular blood, in the hard part or through the hard part.

The medical device further comprises at least one converter. The converter is arranged to measure a characteristic of the medical fluid or of another fluid while it is present in one of the fluid paths. Alternatively or additionally, the converter is arranged to measure a characteristic of the medical device or an effect, such as internal or external pressure, applied to the device.

The medical device further comprises a device to determine a characteristic, in particular a geometric characteristic, of the medical device, in particular, of a fluid path thereof.

The method disclosed herein serves to measure or determine the characteristic of a medical fluid present in the device, e.g. using a converter of the medical device. Alternatively or additionally the method serves to detect or output a value of a characteristic of a fluid, such as a medical fluid. Preferably, it serves to correct a characteristic of the fluid, detected by the converter and its output signals, or to correct the signal.

The method comprises providing a medical device. It further comprises outputting a signal value by means of the converter of the medical device in relation to a characteristic of the fluid, while it is present in one of the fluid paths.

The method disclosed herein also comprises providing the result of a reference-measurement for the characteristic, in particular a geometric characteristic. This result is referred to here as "first value." The reference-measurement which led to this result, can be carried out in advance, i.e. before the commencement of the method. It may be carried out at the factory, prior to delivery to the user etc. but is not limited thereto.

The method further comprises receiving a signal from the device to determine the, in particular geometric, characteristic of the medical device, whereby the signal relates to the, in particular geometric, characteristic. The rate of the signal or its value is referred to herein as "second value".

Finally, the method also comprises outputting a value of the characteristic of the fluid, in particular of the medical fluid, by using a relation between the first value and the second value. Alternatively or additionally, the method further comprises the correction of the signal value using the relation between the first value and the second value.

The evaluation unit or evaluation device as disclosed herein is programmed or configured to carry out the method, optionally in conjunction with a treatment apparatus and a medical device.

The treatment apparatus as disclosed herein comprises a device for receiving or attaching the medical device to the treatment apparatus. The latter device can be or have an actuator-sensor-plate.

The treatment apparatus further comprises a device for providing the result of a reference-measurement for the, particularly geometric, characteristic. This result is referred to herein as the "first value".

The treatment apparatus comprises a device to receive a signal from the device to determine a, particularly geometric, characteristic of the medical device. This receiving-device receives a signal, that relates to the, particularly geometric, characteristic. The signal is herein understood as the "second value".

The treatment apparatus finally comprises a device for the output of a value of the characteristic of the particularly medical fluid, by using a relation between the first and the second value. Alternatively or additionally the treatment apparatus comprises a device for the correction of the signal value by using a relation between the first and the second value.

Alternatively or additionally to the aforementioned devices, the treatment apparatus comprises an evaluation unit.

In all embodiments herein the use of the expression "can be" or "can have" and so on is understood to be synonymous with "is preferably" or "has preferably" and so on and is intended to illustrate an embodiment.

Embodiments may comprise one or several of the aforementioned or following features. In this way, the features mentioned herein may, in any combination thereof, be subject-matter of the embodiments unless the person skilled in the art recognizes a concrete combination as technically impossible. Furthermore, embodiments are subject-matter of the dependent claims.

Whenever numerical words are mentioned herein, the person skilled in the art will recognize or understand them as indications of numerical lower limits. Unless it leads the person skilled in the art to an evident contradiction, the person skilled in the art will comprehend the specification for example of "one" encompassing "at least one". This understanding is also equally encompassed as the interpretation that a numeric word, for example, "one" may alternatively mean "exactly one", wherever this is evidently technically possible for the person skilled in the art. Both are encompassed and apply herein to all used numerical words.

The information "top" and "bottom" are to be understood, in case of doubt by the person skilled in the art, as absolute or relative spatial information which refer to the position of the respective component during its intended use.

When, herein, a device is mentioned which serves to carry out a method step, the device concerned which carries out this step may be respectively configured, programmed, provided and/or equipped.

In some exemplary embodiments, the hard part (being herein also denoted as hard body or as substrate), and/or its accessories like tubes, etc., are to be understood as the part which is usually produced by an injection molding process and therefore referred to herein as "hard" body of the medical device, wherein said hard body may be covered by a comparatively "soft" film. The hard part may be made of PP (polypropylene), PE (polyethylene). PA, ABS, PMMA, PC, PVC or of other polymer sufficiently known to the person skilled in the art or of other materials. It may be made of insulator materials, such as in particular, e.g., ceramic.

The terms sensor and sensor arrangement are used synonymously for a system comprising or consisting of a converter, signal transmission components and/or evaluation unit. The converter is thereby to be understood preferably as a section of the sensor provided on the device side which is in contact with the measuring medium. The converter converts the result of its measurement into suitable signals, e.g. current or voltage signals. The signal transmission components likewise belonging to the sensor arrangement forward the result of their measurement to the evaluation unit, which in the prior art is usually provided on the machine side.

In some, exemplary embodiments disclosed herein, the characteristic of the medical device is a geometric characteristic. The characteristic of the medical device will in the following also be referred to by the short form "characteristic". It may be, but it is not limited to, a geometric characteristic.

In addition, the spatial expansion, the size or the composition/nature of the medical device can also be understood as "characteristic". Furthermore, the material density, and, e.g., derived therefrom, also the quality of the sterilization may be referred to as characteristic. Furthermore, the material color or the chemical properties such as the composition or contained particle are also optionally understood under the term "characteristic". Furthermore, the material strength and/or the wall thickness is also optionally understood as a characteristic of the medical device.

In some exemplary embodiments disclosed herein, the device to determine a characteristic of the medical device, is a device configured and/or programmed and/or designed to determine a, particularly geometric, characteristic of the medical device.

In some exemplary embodiments disclosed herein, the device to identify a characteristic of the medical device, in particular of a fluid path, is a single part or multipart component, which may determine or measure the characteristic In such embodiments the device may, in each case, be a sensor or a converter that emits results of measurements carried out by it or with it. In such embodiments the device may comprise, of each, at least one sensor system, one circuit, one conductor or the like. In such embodiments one could refer to the device as an "active" device.

In some, exemplary embodiments disclosed herein, the device to determine a characteristic of the medical device, in particular of a fluid path, is a single part or multipart component with which the characteristic can be determined or measured. In such embodiments the device may respectively be at least a marker, which can be either optically recognizable using an x-ray or using a further method for proving it existence and/or position and it is in particular provided for this purpose. In such embodiments, one could refer to the device as a "passive" device.

In some exemplary embodiments disclosed herein, the device to determine the characteristic of a medical device is a mark, a marker, a coil, a passive element, a piezo element, an element, which is made of a different material than the hard part and/or the fluid path, an element, that is connected to a voltage source, an element that is connected to a conductive path and/or any combination thereof.

In some exemplary embodiments disclosed herein, the characteristic of the medical fluids is understood to mean, the pressure under which it is subject to, the flow or the flow velocity with which it flows, its temperature, its conductivity and so forth, preferably respectively at e.g. the point of measurement by the converter.

In some exemplary embodiments disclosed herein, the device to determine a characteristic of the medical device, is a device for effecting the medical fluid. It may particularly be designed, in order to induce it to oscillate, while the medical fluid is present in one the fluid paths—and preferably in one that is connection with the converter.

In some exemplary embodiments disclosed herein, the device to determine a characteristic of the medical device, is at least a piezo element or at least comprises such.

The piezo element may also be or comprise a plastic piezo element.

In some exemplary embodiments disclosed herein, at least one section of the converter and/or at least one section of the device to determine a characteristic of the medical device are applied to the hard part by at least one additive application method.

In particular the following methods may be understood by an additive applications method:

Selective Laser Melting (SLM),
Selective Laser Sintering (SLS),
Selective Heat Sintering (SHS),
Binder Jetting (solidification of powder material by binder)
Electron Beam Melting (EBM)
Fused Deposition Modeling (FDM or Fused Filament Fabrication (FFF)),
application welding or cladding,
Wax Deposition Modeling (WDM),
Contour Crafting,
Metal Powder Application methods (MPA),
Cold Gas Injection
Stereolithography (SLA)+micro-SLA,
Methods using Digital Light Processing (DLP) for exposure to light
Liquid Composite Molding (LCM).
Laminated Object Modeling (LOM),
3D screen printing of metals and
Light-controlled electrophoretic deposition.

In some exemplary embodiments disclosed herein, the application method comprises, or is, a template-free application. These can apply to the first, the second and/or further application methods as well as to combinations thereof.

In some exemplary embodiments disclosed herein, a template-free application is to be understood as an application without using a mask or template.

In some exemplary embodiments disclosed herein, the application method is not template ink printing, nor an "ink stencil printing", nor a "screen printing" nor a photolithographic method, in particular, respectively, not in a continuous method.

In some exemplary embodiments disclosed herein, a template-free application is to be understood as a waiver of any layer or bezel, which is to be removed subsequently.

Applying using a template may be understood herein as shadowing or protecting, in a suitable form, of areas which must not be coated. Such application takes place, for example, by bezel (e.g. with spray lacquering etc.) or by lacquer templates (e.g. with wafers, manufacturing circuit boards, etc.).

In some exemplary embodiments disclosed, the medical device comprises a plurality of converters, i.e. two or more, each of which, at least in one section thereof, is directly or indirectly applied to the hard part by an additive application method (or by several additive application methods), preferably a printing method.

In some exemplary embodiments disclosed herein, the application method comprises or consists of applying conductive ink.

Conductive ink is understood here to mean fluids with, e.g., nanoparticles or microparticles which if appropriately tightly applied together form a functional path such as, e.g., a conductive path (also referred to herein as an electrode) through which, i.a., signals may be transmitted. Other materials and aggregate conditions than conductive ink may as well be considered or are included. Ideally, conductive ink may be biocompatible, but does not have to. Additionally or alternatively, living cells, proteins, etc. may be part of the ink rendering it conductive.

The conductive ink or the alternative material may be used in any aggregate conditions. In some embodiments, an aggregate condition may be understood to mean a solid or liquid hydrogel in which a biomarker is incorporated. Frozen (i.e. solid) substances or microencapsulated active ingredients/reagents may also be processed. Paths may also be separated from the gas phase by sublimation/condensation.

Conductive ink is here also to be understood as e.g. liquids which comprise carbon-conductive polymers, metal particles and/or combinations thereof, moreover as metalized ink.

The aerosoljet printing technique known from the prior art (see in this regard EP 2 559 656 A1) is considered as an example for an additive application and, in particular, for printing. The technique disclosed therein and the devices described therein for carrying out this technique are suitable for this purpose, in particular also because of the geometric design of the nozzle tip, which allows the necessary number of degrees of freedom for the movements during the printing process.

The present invention is of course not limited to the use of the aerosoljet. The person skilled in the art recognizes that all additive and/or template-free printing methods, in particular those by means of which conductive ink may be applied in the sense of this description, are encompassed.

In some exemplary embodiments disclosed herein, the at least one converter is a magnetic flow meter.

In some exemplary embodiments disclosed herein, the at least one converter is configured or designed for measuring or determining conductivity, pressure, flow, current or voltage. The value of the signal which is herein denoted to as signal value, which is the output of the converter, may thus be a value which represents or depends on the conductivity, the pressure, the flow, the voltage, the concentration, the current or another measured variable.

A value may be a figure with or without dimension.

In some exemplary embodiments disclosed herein, the medical device is a blood cassette, a blood tube, a blood filter, a tube, a tube system, a tube set or a respective part thereof.

In some exemplary embodiments disclosed herein, the medical device is a disposable.

In some exemplary embodiments disclosed herein, the method comprises no manual calibration, no use of a calibration or gauge unit measure, for example in the form of a reference volume (e.g. with a flow sensor).

In some exemplary embodiments disclosed herein, the step of correcting and/or using the relation between the first and the second value is carried out only in the case that a difference, a ratio or another mathematical relationship between the first value and the second value reaches or exceeds at least one predetermined value.

In some exemplary embodiment disclosed herein, the sections or components applied by one or several additive application methods comprise in addition to the at least one converter at least conductive paths, electrodes, a multipole connector or a plurality thereof, respectively.

The term "medical fluid" includes each medical liquid and/or each medical gas as well as any combinations. The fluid is preferably blood.

In some exemplary embodiments disclosed herein, the same which is stated about the medical fluids relates also to non-medical fluids. The present invention is therefore not limited to medical fluids.

A medical device as disclosed herein may be a disposable component or a disposable article, which is e.g. made of a plastic material.

The medical device as disclosed herein or its hard part may be produced by an injection molding process.

The medical device as disclosed herein may have liquid and/or gas connections, half-open channels and/or chambers. One or more cover elements, such as e.g. membranes or foils, may serve to close and/or seal the channels and chambers.

The blood treatment, for which the medical device is properly used, may, for example, be a dialysis method, a hemodialysis, hemofiltration, hemodiafiltration and the like.

In certain exemplary embodiments disclosed herein, the medical device is a blood cassette. The hard part in such examples is a cassette body or cassette main body or a tubing section.

In certain exemplary embodiments disclosed herein, the medical device further comprises at least two connectors for pump tube segments for peristaltic pumps, with or without the pump tube segments.

In certain exemplary embodiments disclosed herein, the medical device has a single-needle sterile membrane.

In some exemplary embodiments disclosed herein, the same which is stated about the medical device applies also to non-medical devices. The present invention is therefore not limited to medical devices.

In certain exemplary embodiments disclosed herein, the piezo element is a PVDF ("plastic piezo").

In certain exemplary embodiments disclosed herein, the piezo element is applied to the medical device by one of the application methods mentioned herein.

In certain exemplary embodiments disclosed herein, the piezo element. e.g. as PVDF element, is applied by aerosoljet to the medical device.

In certain exemplary embodiments disclosed herein, the piezo element is attached to the inside of the wall of the measuring cell.

In certain exemplary embodiments disclosed herein, the piezo element is attached to the outer side of this wall.

In certain exemplary embodiments disclosed herein, the piezo element serves as both an actuator for inducing oscillations and a sensor, i.e., it alternately receives the reflection of the previously triggered oscillations and converts them into electrical voltage, which can then be evaluated. By measuring the temporal distances of the reflected signals, the size of the measuring cell may be deduced.

In certain exemplary embodiments disclosed herein, a further piezo element is attached to the opposite wall. Here too, the positioning is possible on both the outer side and the inner side of the wall. In this embodiment, the first piezo element serves as an actuator and the second piezo element serves as a sensor. The transmission time or the time span of the induced oscillations is determined. From this, the characteristic of the device can be deduced. In an embodiment, the two piezo elements alternately serve hereby as emitter and sensor.

In certain exemplary embodiments disclosed herein, the device, is not a medical device: the apparatus with the device for receiving or coupling of the device is not a blood treatment apparatus. The present invention is thus not limited to the use as medical technology.

In certain exemplary embodiments disclosed herein, the treatment apparatus is designed as a blood treatment apparatus, in particular an apheresis apparatus or dialysis apparatus, in particular a hemofiltration apparatus, a hemodiafiltration apparatus, a filtration apparatus or an apparatus for extracorporeal gas exchange.

Some or all of the embodiments disclosed herein may have one or more of the advantages mentioned above or in the following.

Modern medical systems for blood treatment usually comprise a blood treatment apparatus (on the so-called "machine side") and medical devices (on the so-called "device side") attachable thereto. If the medical device is a disposable, the so-called "disposable side" is also referred to herein. Although the present invention is not limited to disposables herein, reference is exemplarily made to disposable medical devices also, without being limited thereto. The disposable articles used during a blood treatment session are discarded after the blood treatment session for reasons of hygiene because they came into, or might have come into, contact with the patient's blood.

In order to monitor the treatment, sensors and actuators, which measure parameters on the disposable article or on the medical device or which affect the latter, are required.

Disposables produced inexpensively using injection molding are generally subject to certain manufacturing tolerances which are detrimental to the absolute accuracy of the geometric or dimensional properties or dimensions of the disposables.

Medical disposables often have measuring cells, the exact dimensions of which have an influence on the measurements made herein. This applies in particular to functionalized or partially functionalized disposables which carry sensors or converters, and also applies to medical disposables.

Even when affecting medical disposables by actuators, there are situations known, in which the exact dimensions of the disposable or of a certain section thereof have influence on the control or the drive of an actuator.

It is known in the state of the art to calibrate such medical disposables by individual measuring ex-works. For this purpose, each individual measuring cell is examined immediately after production, e.g., by spatial measurement or volume determination, or the like. The measurement data is subsequently delivered with the product, e.g., the medical disposable, e.g., stored on a storage medium. With this measurement data, the medical disposable may be calibrated at the location of use respectively on the treatment apparatus which has been equipped with the medical disposable. This method however has some disadvantages. On the one hand, there is no correction of geometry or material changes such as, e.g., deformations caused by falling, sun exposure, etc., which occur after the a.m. initial measuring. Furthermore, the method is logistically complex and requires with this calibration step a further processing step at the location of the production of the medical disposable, which increases its production costs.

Moreover, due to the manufacturing tolerances of a medical disposable article, no single general calibration may be carried out for all related components or disposables of one type. The absolute calibration based on such general data regularly leads to a too inaccurate measuring in the case of a sensor or to a too inaccurate control in the case of an actuator. The necessary individual calibration of each related component is thus rendered or made more difficult.

An example for a sensor whose measurement result depends significantly on the exact information about the spatial size of its measuring cell, is for instance a magnetic flow meter. In this, the measurement results depend directly on the size of the cross-sectional area of the fluid path in the region of the measuring electrode. An example in the field of actuators is the drive of a magnetically driven and/or magnetically mounted impeller pump in the medical disposable.

Herewith the present disclosure may advantageously provide corrective measures. The effect of a change which has taken place after leaving the place of manufacturing, for example a change of the geometry of the disposable, may be compensated on a measuring signal.

However, the person skilled in the art will appreciate that the application of the present invention is not limited to these examples but relates to all types of sensors or actuators in or on substrate bodies which are subject to manufacturing tolerances and whose precise spatial dimensions are therefore a priori not sufficiently known. Although such applications are advantageously applicable in particular to medical methods and the disposable articles used there, the present invention is not limited to the field of medical technology.

Further advantages encompass the following:

A functionalization of the disposable itself, i.e., the integration of the whole sensor system necessary for monitoring a specific parameter in the disposable, has so far been found to be economically unprofitable because the comparatively expensive sensor components would be discarded after each use. Therefore, conventional disposables for medical blood treatment are usually very simple, essentially consisting of the tube for the passage of the blood. For the above-mentioned reason, they usually do not carry sensors.

Consequently, these sensors and actuators are provided in the state of the art largely on the machine side. From there, they affect or are in interaction with the medical device via a plurality of sensor and/or actuator interfaces. These interfaces generally determine the form factor or design and lead to the fact that medical systems of the prior art cannot be embodied arbitrarily small.

On the other hand, for the first time the devices and methods described herein now make it advantageously possible to provide a cost-effective and thus economical alternative to the functionalization of medical devices as well as of disposables. This advantageously allows the miniaturization of the systems used, e.g. blood treatment systems. Their miniaturization is desirable not least because it contributes to the reduction of both the extracorporeal blood volume and the effort required for extracorporeal conveyance and hydraulics.

In contrast to the state of the art, in which the functionalization was attempted by the integration of the individual sensor components into the disposables with the a.m. disadvantages, the present invention, as described supra, provides a solution for the effective shift positioning of sensor components on the medical device.

It is also advantageous that the methods disclosed herein, in which all sensor components arranged on the device side, may be integrated in the same production method. This may further reduce the production efforts.

A complete functionalization or only a partial functionalization of the device may reduce the cost per disposable as the device can be discarded together with the converter without significant economic loss due to the particular manner with which the converters are shifted to the device.

For example, with respect to a converter, a partial functionalization is understood to mean that the core task of the converter, i.e. detecting a physical, chemical or other parameter or value as well as converting this parameter into an electromagnetically transferrable substitute value, takes place on the medical device itself, either invasively (i.e. in contact with blood or a treatment liquid) or non-invasively. However, e.g. the processing of the signal as well as and the interpretation as well as further steps, requiring more sophisticated. e.g. integrated electrical components, are carried out on the machine side. However, in some cases, some or all of the signal processing may also be carried out completely on the machine side. In the latter embodiment, a complete functionalization is mentioned: at least one sensor arrangement or one sensor, is completely additively applied to the device. In this, the device-side components of a sensor arrangement or of a sensor may be applied using the same template-free and additive production methods as described supra.

It is also advantageous that disposables disclosed herein, when equipped with individual complete sensors, may thus be fully functionalized. The herein-presented method for applying converters or other components of sensors makes this possible.

The partial functionalization and, hence, the remain of the complex electronics necessary for the post-processing and evaluation of the signals on the machine side is therefore advantageous in that the often simpler-designed components of the respective sensors which are applied by the same additive and template-free printing technology are arranged on the device Furthermore, the functionalization is economically advantageous, since the production can be made extremely cost-effective by the common use of the same production technology, for example in the same production step for all sensor components arranged on the device side.

Since the production method disclosed herein is preferably an additive, template-free printing method, a modified version of the device, e.g. with new sensor geometries, may optionally even be produced by just simply loading or installing the corresponding data record in the software. There is no need to make changes in the production hardware, such as, e.g. the purchase of an injection mold, which would be necessary in the production of the medical device by means of injection molding. This aspect, too, leads to simplified manufacturing and improved cost-effectiveness.

A further advantage with regard to conventional (non-functionalized) systems is that the physical or chemical parameter to be measured does not need to be guided mechanically to the machine side, as it is the case. e.g., with known pressure sensors within which the pressure conditions to be measured are guided via a pneumatic line to a measuring membrane which is not disposable and arranged on the machine side. In order to protect said membrane from liquid, complex protective membranes are required regularly, which are referred to as transducer protector (TP). All mechanical interfaces to the machine may thus be omitted. All parameters to be measured may be converted at least into analogue electromagnetic signals (current, voltage, optical signals) by the integrated parts of the sensor system, and may be transmitted only in this form to the processing and evaluation unit on the machine side. For coupling the entire device-side sensor system, only one corresponding multi-channel electromagnetic and/or optical interface is required (multi-connecting device), which allows a significant reduction of the latter.

BRIEF DESCRIPTION OF THE FIGURES

In the following, the present invention is described with reference to the accompanying drawings. In the drawings, identical reference numerals denote similar or identical elements. The following applies.

DETAILED DESCRIPTION OF THE FIGURES

Figure 1:
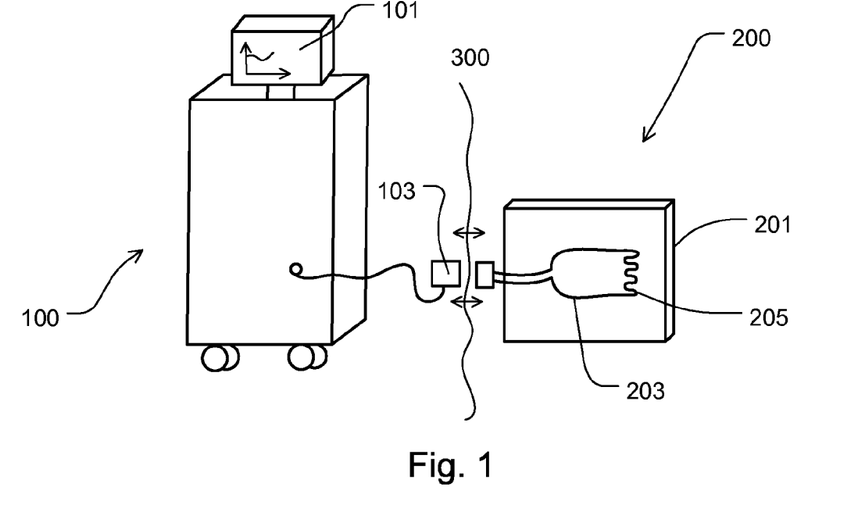
FIG. 1 shows a medical system for blood treatment with a medical device as a partially functionalized disposable.

FIG. 1 shows a very schematic and only exemplary blood treatment apparatus 100 as an example of a treatment apparatus, with a medical device 200 (in short: device 200 cf) as an example of a disposable medical device.

The device 200 is exemplarily designed as a disposable. The device 200 is partially functionalized, purely optionally, by means of an additive, template-free printing method.

The blood treatment apparatus 100 and the device 200 are connected to each other via an interface 300 in signal communication.

The device 200 comprises a hard part 201. Parts of a sensor arrangement, here a conductive path 203 and a converter 205, are provided on the hard part 201.

The converter may be, for example a pressure transducer. The converter can be printed on the hard part 201. On the disposable side, the converter can only convert the parameter of pressure to be measured into an analogue electrical signal.

Figure 5:
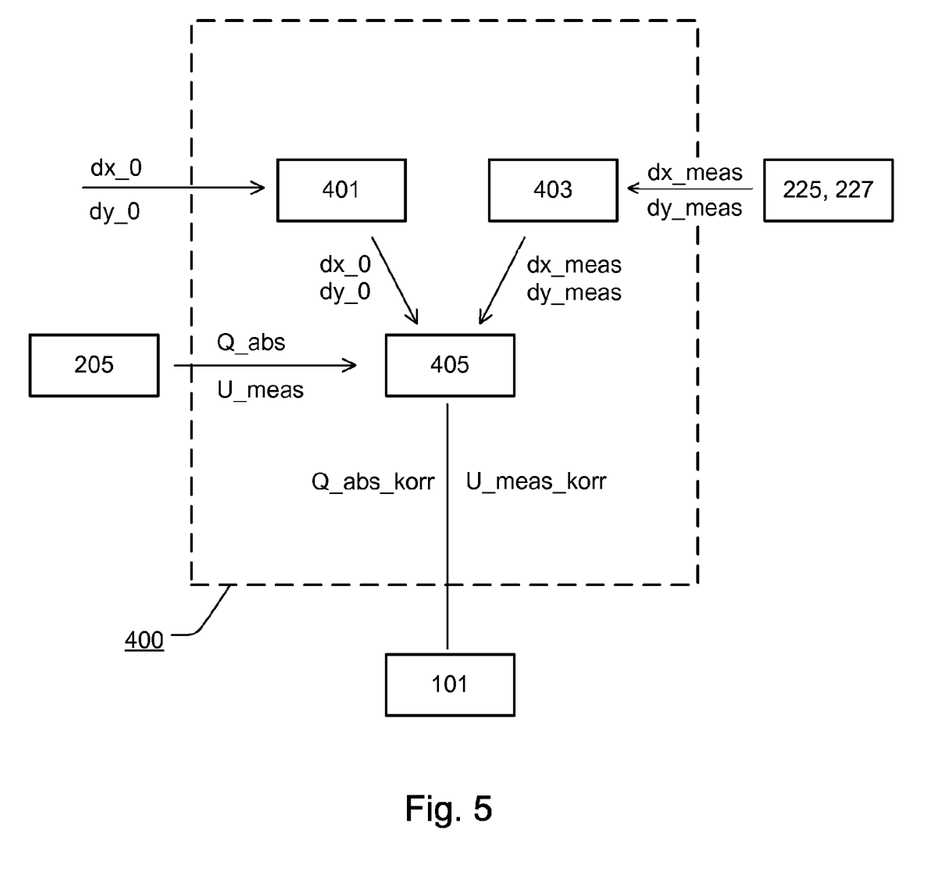
FIG. 5 shows an exemplary embodiment of an evaluation unit.

The electrical signal is conducted via the—also optionally additively printed—conductive path 203 to the defined interface 300, which is connected to a machine-side evaluation unit 400. The evaluation unit 400, which is described further in FIG. 5, is represented in FIG. 1 by a monitor 101 for displaying the evaluation results obtained from it.

On the machine side the signal can be digitalized, by means of an AD (Analogue-to-digital) converter (short form ADC) 103. Post-processing steps (filtering, smoothing, Fourier transformation, zero filling etc.) may take place prior to a final evaluation and interpretation. All these optional steps may be carried out, for example, in the evaluation unit 400.

Figure 2:
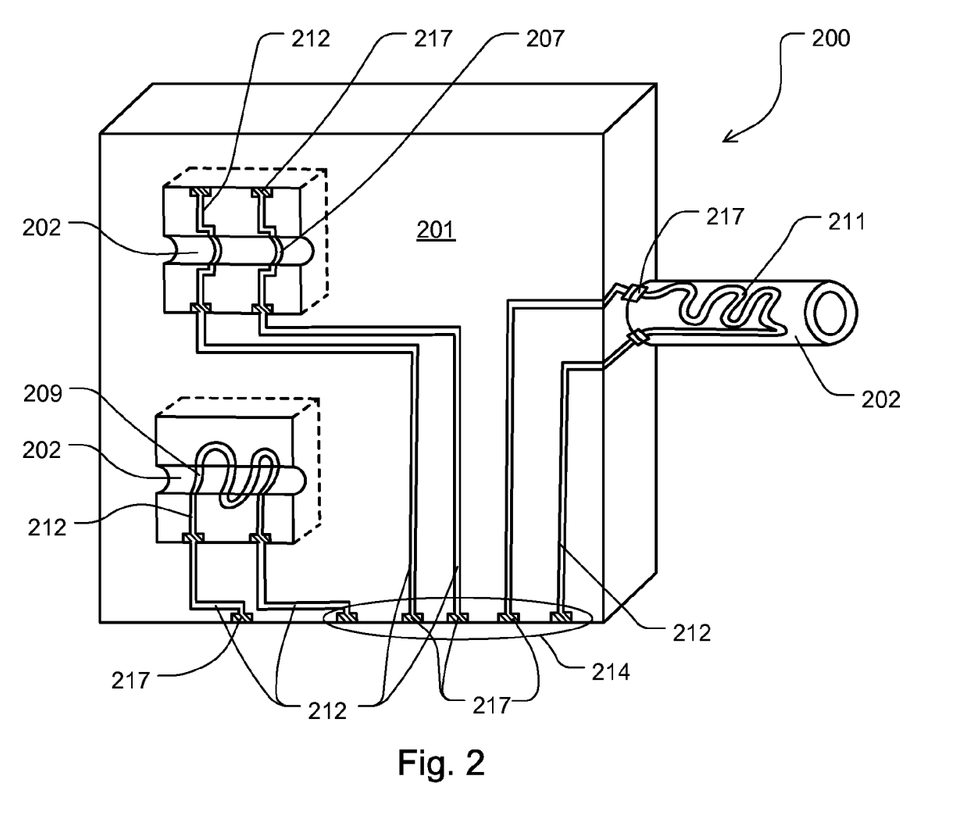
FIG. 2 shows a medical device according to a second exemplary embodiment.

FIG. 2 shows a medical device 200 according to a second exemplary embodiment.

The medical device 200 is a partially functionalized disposable with three different converters 207, 209, 211.

Thereby FIG. 2, along with the following figures, shows each example of applied converters 207, 209, and 211 and conductive path 212, whereby converter and conductive path were applied by means of different application methods or by the same application method. Alternatively, at least one of the converters 207, 209, and 211 one of the conductive paths 212, have been each applied by means of more than one application method—but at least by a first and a second application method.

A converter 207 for measuring the conductivity is arranged in the upper left of FIG. 2. The converter consists of two conductive paths, which are applied in the interior of a fluid-conducting channel 202 of the device 200 by the additive, template-free printing method.

The two other converters 209, 211 show exemplary embodiments of pressure transducers. These can be arranged as strain gauges on the inner contour (see the converter 209) or on the outer contour (see the converter 211) on the fluid-conducting channel or tube 202 of the device 200.

Besides the converters 209, 211, FIG. 2 shows the electromagnetic signal guidance with conductive and contact 217 paths 212 towards the machine interface 300, here exemplarily a multipole connection device 214. The conductive paths 212 towards the signal line may be applied onto the planar surface of the hard part 201 with the same additive and template-free method, in particular, in the same process step.

However, non-planar (three-dimensional) line guidance, in the sense described supra, or crossings of (correspondingly insulated) lines are also possible.

The conductive paths 212 as well as the contacts 217 may also be applied by a second, additive and template-free printing method, e.g. in a second production step which follows the application of the converters 207, 209, 211. The entirety of the conductive paths 212 used to guide signals from the location of the respective converters 207, 209, 211, which converts the variable to be measured e.g. into an electro-magnetic signal that is guided by means of the conductive path 212 towards machine interface 300, may also contain individual parts, which are applied by a two-component injection molding of conductive polymers.

Figure 3:
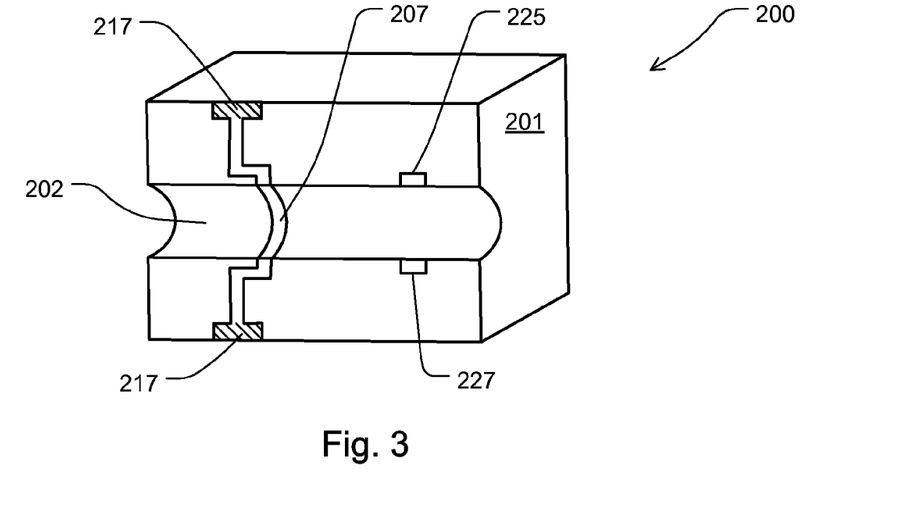
FIG. 3 shows a section of the fluid-conducting channel or the tube of the hard part of the device with a device to determine a characteristic of a medical device, in particular of a fluid path in a first embodiment.

FIG. 3 shows a section of the fluid conducting channel or tube 202 of the hard part 201 of the device 200 with a device to determine a characteristic of a device, here a geometric characteristic of the medical device 200, in particular of the fluid path 202, in a first embodiment.

The converter 207 may be a part of the magnetic flow meter, which measures the flow through channel 202.

The channel 202 may comprise a circular, rectangular, or another cross-sectional form or basic shape on the area of converter 207. This particularly applies for the area in which the converter 207 is present, for example, the measuring cell.

The device 200 comprises, in this exemplary embodiment, at least two piezo elements or electromagnets 225, 227. These may be understood as an example of a device to determine the characteristic of a medical device 200 or of a part thereof. The piezo elements or electromagnets 225, 227 are optionally here arranged as coils. The coils optionally lie on or at opposite sides of the measuring cell.

The device to measure a characteristic of the medical device 200 may in each embodiment be the converter 207, part of the converter, or provided independent of these.

Figure 4:
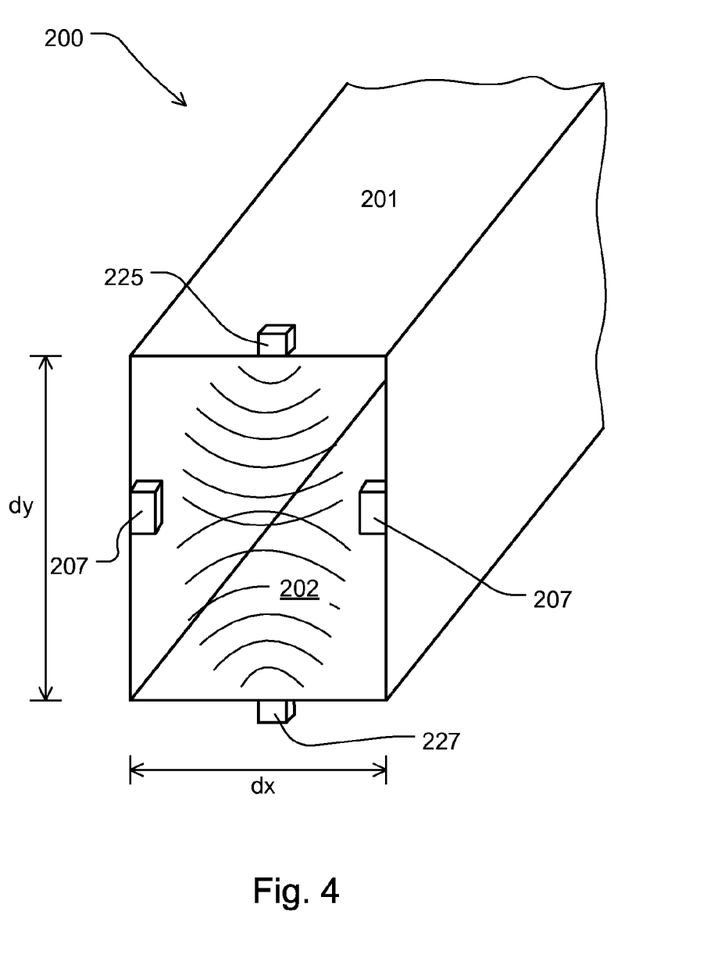
FIG. 4 shows a section of the fluid-conducting channel or the tube of the hard part of the device with a device to determine a characteristic of a medical device, in particular of a fluid path in a second embodiment.

FIG. 4 shows a view into a section of the fluid conducting channel or tube 202 of the hard part 201 of the device 200 (here a disposable) in a second embodiment. The device 200 comprises a device to determine a (geometrical) characteristic of a medical device 200, in particular of the fluid path 202.

The channel 202 has a rectangular cross-sectional form or basic form, in the area of the measuring cell.

The device 200 comprises at least two piezo elements or electromagnets 225, 227. These are again optionally designed as coils. The coils optionally lie on or at the opposite sides of the measuring cell.

These coils 225, 227 are arranged on the machine side, however, the measuring cell of the medical device 200 is inserted in such a way between the coils 225, 227 that it will be penetrated by a largely homogeneous magnetic field. The measuring electrodes of the converter 207 are arranged perpendicular to the connecting axis of both coils 225, 227 (magnet field direction). These are positioned invasively, for example in direct contact with the fluid to be measured. Hereto they reach through the channel wall into the fluid path 202 or are printed on the channel wall of the fluid path 202.

The evaluation unit 400 (see FIG. 5) is provided on the machine side, or on the device 200 The device 200 shown in FIG. 4 functions to determine a characteristic of the medical fluid depending on a signal value, which is determined by the converter 207 . . . . The function may be a generic type-specified calibration. This may apply to the corresponding converter-device/disposable-combination. In the present example, calibration represents a function, which indicates the present flow for the respective measurement value, for example, the measured voltage at the measuring electrodes of the converter 207. The evaluation unit 400 may use the signal value or characteristic of the medical fluid in later evaluations $$Q\_abs = f(U\_meas)$$

The above-mentioned, exemplary calibration function f is, amongst others, linearly dependent on the cross section of the measuring cell. While the deviations from a set-point, which are caused by manufacturing or handling, do not strongly influence the accuracy of the calibration in the axis of the measuring electrodes i.e. of the diameter dx perpendicular to the magnetic field indicated in FIG. 4, deviations from a set-point dy_0 of the diameter dy, that is the axis parallel to the magnetic field can lead to a significant malfunction in the absolute-calibration if they are not corrected.

The device 200 can therefore provide for the example shown herein in FIG. 4 that the distance of the walls of the measurement cell is verified in y-direction by the device 403 of the evaluation unit 400 shown in FIG. 5 to determine a characteristic of the medical device 200, at least in the axis of the magnet field in situ taking into consideration its deviation from the target distance dy_0. The interval may be stored or readable as the result of a reference measurement.

If a correction is found to be necessary e.g. due to the difference between the interval/desired distance dy_0, so may a correction of the calibration be made regarding absolute flow values. In this way, the necessary accuracy of the measurement can be ensured even with measurements at disposables by injection molding which are by nature subject to manufacturing tolerances.

For example, for these corrections, the above calibration formula f with the ratio of actually measured diameter dy_meas as a second value and the target/desired diameter dy_0 of the fluid channel as the first value may be multiplied or otherwise taken into account as follows:

$$Q\_abs\_korr = f(U\_meas) * (dy\_meas / dy\_0)$$

Alternatively the signal U_meas could be suitably corrected.

In FIG. 4, a Piezo element 225, 227 can be induced to oscillate to determine the actual diameter dy_meas as a second value.

FIG. 5 shows an exemplary embodiment of an evaluation unit 400, which is programmed and/or configured to carry out the method.

The evaluation unit 400 may be part of the blood handling apparatus 100. Alternatively, it may be provided independent of this. As discussed in the following in the example of FIG. 5, devices to carry out the methods are part of the evaluation unit 400. They could alternatively be part of the blood handling apparatus 100 or another unit, which is not evaluation unit 400.

FIG. 5 shows a device 401 for providing the result of a reference measurement or—determination of a geometric characteristic dx, dy as a "first value". The result of the reference measurement may herein be an example of the extension in x-direction and/or in y-direction. The result in FIG. 5 is therefore not restrictively referred to as dx_0 respectively dy_0. The first value may be stored in the device 401, it may alternatively be stored in a further device inside or outside of the evaluation unit 400. Alternatively, it may be read out by the medical device 200, e.g. as it is held as a bar code or by a label on the medical device 200.

FIG. 5 further shows a device 403 to receive a signal from the device to determine the geometric characteristic dx, dy of the medical device 200, e.g. from one or both of the piezo elements 225, 227 whereby the signal relates to the geometric characteristic dx, dy. In the following considerations, the signal is referred to as "second value".

FIG. 5 further shows a device 405 which has to output a value Q_abs_korr of the characteristic Q of the medical fluids or a corrected signal value U_meas as output. Both value Q_abs_korr or a corrected signal value U_meas are determined or corrected by using a relation between the first value dx_0, dy_0 and the second value dx_meas, dy_meas.

The device 405 may be connected with the monitor 101 or with another display device via signal connection to display the value Q_abs_korr of the characteristic Q of the medical fluids or the corrected signal value U_meas.

LIST OF REFERENCE NUMERALS 100 blood treatment apparatus
101 monitor
103 AD-converter
200 blood cassette as an example of a medical device
201 cassette body or cassette main body, hard part; hard body
202 fluid path, channel, flow channel
203 conductive path, conductor or signal conductor
205 converter
207 converter
209 converter
210 converter
211 DMS element as a converter
212 conductive path, conductor or signal conductor
217 contacts
225, 227 piezo element or electromagnets
300 interface, machine interface
400 evaluation unit
401 device for providing the results of a reference measurement or reference determination for the characteristic 403 device for receiving a signal from the device for determining a characteristic (dx, dy) of the medical device
405 device for outputting a value (Q_abs_korr) of the characteristic

The invention claimed is:

1. A medical device configured to be received by or attached to a blood treatment apparatus, the medical device comprising:
a hard part defining fluid paths for conducting a medical fluid through the hard part;
at least one converter, wherein the at least one converter is arranged to measure a characteristic of the medical fluid while the medical fluid is present in a particular fluid path of the fluid paths; and
a sensor configured to determine a characteristic of the medical device,
wherein:
the characteristic of the medical device is: (i) a spatial expansion, (ii) a composition of the medical device, (iii) a density of a material of the medical device, (iv) a quality of sterilization, (v) a material color, (vi) a chemical property, (vii) a material strength, or (viii) a wall thickness;
the at least one converter is configured to transmit a signal value related to the characteristic of the medical fluid to the blood treatment apparatus;
the signal value is corrected based on a relationship between a diameter of the particular fluid path measured by the sensor in a direction parallel or perpendicular to a magnetic field and a reference value for the diameter of the particular fluid path, and
the characteristic of the medical fluid is determined based on the signal value that is corrected.

2. The medical device according to claim 1, wherein the sensor configured to determine the characteristic of the medical device comprises a device for acting on the medical fluid to make the medical fluid swing while the medical fluid is present in one of the fluid paths.

3. The medical device according to claim 1, wherein the sensor configured to determine the characteristic of the medical device comprises at least one piezo element.

4. The medical device according to claim 3, wherein the at least one piezo element comprises a plastic piezo element.

5. The medical device according to claim 1, wherein at least one section of the at least one converter and at least one section of the sensor configured to determine the characteristic of the medical device is applied by at least an additive application method.

6. The medical device according to claim 5, wherein the additive application method includes at least one of: a template free application and a conductive ink application.

7. The medical device according to claim 1, wherein at least one section of the at least one converter or at least one section of the sensor configured to determine the characteristic of the medical device is applied by at least an additive application method.

8. The medical device according to claim 7, wherein the additive application method includes at least one of: a template free application and a conductive ink application.

9. The medical device according to claim 1, wherein the at least one converter is a MID flow sensor.

10. The medical device according to claim 1, wherein the at least one converter is configured or designed to measure or determine a conductivity, flow, pressure, tension or current of the medical fluid.

11. The medical device according to claim 1, wherein the medical device is a blood cassette, a blood tube, or a blood filter.

12. The medical device according to claim 1, wherein the medical device is a disposable.

13. The medical device according to claim 1, wherein the characteristic of the medical device relates to a fluid path of the medical device.

14. The medical device according to claim 1, wherein the sensor comprises at least two coils.

15. A method comprising:
outputting a signal value corresponding to a characteristic of a medical fluid using at least one converter of a medical device, wherein the medical device comprises:
a hard part defining fluid paths for conducting the medical fluid through the hard part;
the at least one converter, wherein the at least one converter is arranged to measure the characteristic of the medical fluid while the medical fluid is present in a particular fluid path of the fluid paths and the at least one converter is configured to transmit the signal value related to the characteristic of the medical device to a blood treatment apparatus; and
a sensor configured to determine a characteristic of the medical device, wherein the medical device is configured to be in signal communication with the blood treatment apparatus;
providing a reference value for a diameter of the particular fluid path;
receiving a signal from the sensor, the signal indicating the diameter of the particular fluid path measured by the sensor in a direction parallel or perpendicular to a magnetic field, wherein the characteristic of the medical device is: (i) a spatial expansion, (ii) a composition of the medical device, (iii) a density of a material of the medical device, (iv) a quality of sterilization, (v) a material color, (vi) a chemical property, (vii) a material strength, or (viii) a wall thickness; and
correcting the signal value using a relationship between the diameter of the particular fluid path measured by the sensor in the direction parallel or perpendicular to the magnetic field and the reference value for the diameter of the particular fluid path.

16. The method according to claim 15, further comprising outputting a value of the characteristic of the medical fluid based on the signal value that is corrected.

17. The method according to claim 15, wherein correcting the signal value comprises determining that a difference between the reference value and the diameter of the particular fluid path measured by the sensor has reached at least a predetermined difference.

18. A medical apparatus comprising:
a blood treatment apparatus; and
a medical device for conducting a medical fluid through the medical device, wherein the medical device is configured to be in signal communication with the blood treatment apparatus, the medical device comprising:
a hard part defining fluid paths for conducting the medical fluid through the hard part; and
at least one converter, wherein the at least one converter is arranged to measure a characteristic of the medical fluid while the medical fluid is present in a particular fluid path of the fluid paths and the at least one converter is configured to transmit a signal value corresponding to the characteristic of the medical fluid to a blood treatment apparatus; and
a sensor that is used for determining a characteristic of the medical device, wherein the characteristic of the medical device is: (i) a spatial expansion, (ii) a composition of the medical device, (iii) a density of a material of the medical device, (iv) a quality of sterilization, (v) a material color, (vi) a chemical property, (vii) a material strength, or (viii) a wall thickness;
wherein the blood treatment apparatus is configured to perform operations comprising:
receiving, from the at least one converter, the signal value corresponding to the characteristic of the medical fluid present in the particular fluid path of the fluid paths;
receiving a reference value for a diameter of the particular fluid path;
receiving a signal from the sensor, the signal indicating the diameter of the particular fluid path measured by the sensor in a direction parallel or perpendicular to a magnetic field; and
correcting the signal value using a relationship between the diameter of the particular fluid path measured by the sensor in the direction parallel or perpendicular to the magnetic field and the reference value for the diameter of the particular fluid path.

19. The medical apparatus according to claim 18, wherein the operations further comprise outputting a value of the characteristic of the medical fluid based on the signal value that is corrected.

20. The medical apparatus according to claim 18, wherein the at least one converter is configured or designed to measure or determine a conductivity, flow, pressure, tension or current of the medical fluid.

* * * * *